US009683964B2

(12) United States Patent
Park et al.

(10) Patent No.: US 9,683,964 B2
(45) Date of Patent: Jun. 20, 2017

(54) TRAPPING ION MOBILITY SPECTROMETER WITH PARALLEL ACCUMULATION

(71) Applicant: Bruker Daltonik GmbH, Bremen (DE)

(72) Inventors: Melvin Andrew Park, Billerica, MA (US); Michael Schubert, Bremen (DE)

( * ) Notice: Subject to any disclaimer, the term of this patent is extended or adjusted under 35 U.S.C. 154(b) by 27 days.

(21) Appl. No.: 14/614,456

(22) Filed: Feb. 5, 2015

(65) Prior Publication Data
US 2016/0231275 A1 Aug. 11, 2016

(51) Int. Cl.
*H01J 49/00* (2006.01)
*G01N 27/62* (2006.01)
*H01J 49/06* (2006.01)

(52) U.S. Cl.
CPC .......... *G01N 27/622* (2013.01); *H01J 49/004* (2013.01); *H01J 49/0031* (2013.01); *H01J 49/06* (2013.01); *H01J 49/061* (2013.01)

(58) Field of Classification Search
CPC .... G01N 27/00; G01N 27/622; G01N 27/624; H01J 49/00; H01J 49/02; H01J 49/0031
USPC ................. 250/281, 282, 283, 290
See application file for complete search history.

(56) References Cited

U.S. PATENT DOCUMENTS

| 3,986,111 A * | 10/1976 | Sellers | G01N 27/62 250/282 |
| 7,838,826 B1 | 11/2010 | Park | |
| 2009/0173877 A1 * | 7/2009 | Bateman | G01N 27/622 250/282 |
| 2009/0294662 A1 * | 12/2009 | Belov | H01J 49/066 250/291 |
| 2011/0121170 A1 * | 5/2011 | Park | G01N 27/622 250/282 |
| 2011/0303838 A1 * | 12/2011 | Green | H01J 49/4265 250/282 |
| 2012/0286156 A1 * | 11/2012 | Park | G01N 27/622 250/282 |

FOREIGN PATENT DOCUMENTS

GB WO 2014140579 A1 * 9/2014 ........... G01N 27/622

OTHER PUBLICATIONS

Eiceman et al., Ion Mobility Spectrometry, Third Edition, 1 Jan. 2013, pp. 91-117.
Kelly et al., The Ion funnel: Theory, implementations, and applications, Mass Spectrometry Reviews, vol. 29, Apr. 23, 2009, pp. 294-312.

* cited by examiner

Primary Examiner — Jason McCormack
(74) Attorney, Agent, or Firm — Benoit & Cote, Inc.

(57) ABSTRACT

The invention relates to the operation of trapping ion mobility spectrometers based on pushing ions by a gas flow against a counter-acting electric DC field barrier, preferably in combination with a mass analyzer as ion detector. The invention provides an additional RF ion trap upstream of the trapping ion mobility spectrometer, wherein the RF ion trap is operated as an accumulation unit in parallel with the trapping ion mobility spectrometer such that a first group of ions can be analyzed in the trapping ion mobility spectrometer while a second group of ions from an ion source are simultaneously collected in accumulation unit.

21 Claims, 3 Drawing Sheets

TRAPPING ION MOBILITY SPECTROMETER WITH PARALLEL ACCUMULATION

BACKGROUND OF THE INVENTION

Field of the Invention

The invention relates to devices and methods for the acquisition of mass spectra of ions separated by their mobility.

Description of the Related Art

In document U.S. Pat. No. 7,838,826 B1 (M. A. Park, 2008), a relatively small ion mobility spectrometer is presented which is termed "trapped ion mobility spectrometer" (TIMS). The length of the essential mobility separation unit, the separator tunnel, amounts to about five centimeters only, not counting additional entrance and exit funnels. The separation of ions according to their mobilities is based upon a gas flow in the cylindrical separator tunnel which drives the ions from an ion source in an accumulation phase against a counter-acting electric DC field barrier while the ions are radially confined by a quadrupolar RF field. After shutting down the delivery of further ions, a scan phase starts, in which the electric DC field barrier is steadily decreased. Ions are driven in the scan phase by the gas flow over the decreasing electric DC field barrier, thereby releasing, successively, ions from low mobilities to higher and higher mobilities from being trapped by the barrier. The ions can be detected in an ion detector, resulting in a mobility spectrum.

FIG. 1 schematically shows a preferred design and operation of a trapping ion mobility spectrometer as described in U.S. Pat. No. 7,838,826 B1. The tube-like separator tunnel (11) between entrance funnel (10) and exit funnel (12) amount to only 48 millimeters in length; the inner diameter amounts to eight millimeters. The ion mobility separator tunnel (11) consists of a series of segmented diaphragms with quadrant electrodes (1), (2), (3), and (4), for generating a quadrupolar RF field. Ions (6) from a source (not shown) are introduced by capillary (8) together with a gas stream (7) into a first vacuum chamber. A repeller plate (9) directs the ions into the funnel (10); the gas flow (14) drives the ions into the separator tunnel (11). In the bottom part of FIG. 1, electric field profiles E(z) along the z-axis are shown for three phases of operation: In the accumulation phase (A) ions are blown by the gas flow (16) against the rising edge of the electric field profile between z locations (20) and (23). In a trap phase (B) of only one to two milliseconds, the inflow of ions is stopped and ions assume their equilibrium position on the rising edge according to their mobility. The steadily decreasing profile voltage in the scan phase (C) releases ions in the order of increasing ion mobility over the plateau of the electric field between locations (23) and (24) and through the exit funnel towards an ion detector. Particularly, the ions may be measured by a mass spectrometer, e.g. a time-of-flight mass spectrometer, resulting in a two-dimensional mass-mobility spectrum. Unlike many other trials to build small ion mobility spectrometers, the device by M. A. Park has already achieved ion mobility resolutions up to $R_{mob}=250$, a very high ion mobility resolution never achieved by conventional mobility spectrometers.

There is still a need for devices and methods operating with highest utility rates (duty cycle) of the ions generated in an ion source of a mass spectrometer, thereby reducing the restriction of the mobility resolution, in particular with an electrospray ion source coupled to liquid chromatography for analyzing complex samples in the field of bottom-up proteomics.

SUMMARY OF THE INVENTION

In a first aspect, the invention provides a method for operating a trapping ion mobility spectrometer, comprising the steps: (a) accumulating ions from an ion source in an RF ion trap; (b) transferring at least a subset of the accumulated ions into a trapping ion mobility separator, in which the transferred ions are radially confined by an RF field and are pushed by a gas flow against a rising edge of a first axial electric DC field barrier such that the transferred ions are spatially separated along the rising edge according to ion mobility; and (c) acquiring an ion mobility spectrum of the transferred ions by decreasing the height of the electric DC field barrier while ions from the ion source are further accumulated in the RF ion trap.

The utilization rate of ions produced in an ion source, accumulated and subsequently separated in an trapping ion mobility spectrometer known from the prior art is limited by the ratio $q=t_a/(t_a+t_s)$ wherein $t_a$ is the ion accumulation time in the trapping ion mobility separator and $T_s$ is the scan time of the electric DC field barrier, during which ions cannot be accumulated in the trapping ion mobility separator. The utilization rate is also termed "duty cycle" here. According to the present invention, the duty cycle can be close to 100 percent when no ions get lost in the RF ion trap (accumulation unit) and in the trapping ion mobility separator (scan unit).

In one embodiment, the ions are radially confined in the trapping ion mobility separator by a quadrupolar RF field. The ions can be accumulated in a RF funnel located between the ion source and the trapping ion mobility separator wherein the field at the exit of the RF funnel is preferably adjusted to the quadrupolar RF field at the entrance of the trapping ion mobility separator. The ions are preferably accumulated in a linear RF trap having a quadrupolar RF field for radially confining the ions. RF fields with higher multipoles, like a hexapolar or octopolar RF fields, can further enhance the ion storage capacity of the linear RF ion trap, but it is more elaborate to couple them with the preferred quadrupolar RF field of the trapping ion mobility separator.

In another embodiment, steps (b) and (c) are repeated to acquire a series of ion mobility spectra, in particular a time series of ion mobility spectra. The ion density can be determined as a function of ion mobility from one or more preceding ion mobility spectra and then used to adjust the electric field profile of the rising edge of the first electric DC field barrier in order to minimize ion losses in the trapping ion mobility separator during steps (b) and (c). The electric field profile is preferably adjusted such that ions are decompressed where a high ion density is determined or where ions of interest are determined.

The ions can be axially trapped at the exit of the RF ion trap by applying a repelling DC potential to an exit electrode of the RF ion trap during steps (a) and (c). Preferably, the accumulated ions are pushed by the gas flow against a rising edge of a second axial electric DC field barrier located in the RF ion trap. During steps (a) and (c), the height of the second DC field barrier is adjusted such that ions are trapped along the rising edge of the second DC field barrier and spatially separated according to ion mobility. In step (b), at least a subset of the accumulated ions is transferred into the trapping ion mobility separator by reversing, turning-off or decreasing the height of the second electric field barrier. The electric field profile of the rising edge of the second electric DC field barrier can also be adjusted to minimize ion losses in the RF ion trap during steps (a) and (c), in particular after determining the ion density as a function of ion mobility from one or more preceding ion mobility spectra.

In another embodiment, the transferred ions are further analyzed in a mass analyzer being located downstream of the trapping ion mobility separator. The transferred ions are preferably fragmented in a fragmentation cell located downstream of the ion trapping mobility separator wherein the fragments ions are analyzed in a mass analyzer located downstream of the fragmentation cell. Precursor ions can be selected in an additional mass analyzer located between the trapping ion mobility separator and the fragmentation cell and then fragmented in the fragmentation cell.

In a second aspect, the invention provides a system comprising an ion source, an RF ion trap and a trapping ion mobility separator. The trapping ion mobility separator comprises an RF field for radially confining ions, an axially acting electric DC field barrier having a rising edge with an increasing electric DC field and a gas flow counter-acting the electric DC field at the rising edge. The RF ion trap (accumulation unit) is located between the ion source and the trapping ion mobility separator and has a first mode of operation for accumulating ions from the ion source and a second mode of operation for transferring ions towards the trapping ion mobility separator.

In one embodiment, the RF ion trap (accumulation unit) is an RF funnel or a linear RF ion trap. The linear RF ion trap is preferably aligned along a common axis with the ion trapping mobility separator wherein both, the linear RF ion trap and the trapping ion mobility separator, comprise a tube for radially confining the gas flow along the common axis. The linear ion trap can be designed as an upstream extension of the trapping ion mobility separator having a length of more than three centimeters, more preferably of more than five centimeters, up to ten centimeters. The linear RF ion trap can be composed of segmented diaphragms with quadrant electrodes as shown in FIG. 1. The inner diameter of the linear ion trap is preferably adjusted to the inner diameter of the trapping ion mobility separator. Preferably, the radially confining RF fields of the linear RF ion trap and the trapping ion mobility separator are substantially quadrupolar.

The linear RF ion trap can comprise an electric DC field barrier having a rising edge with an increasing axial electric DC field. The slope (axial gradient) of the electric field strength along the rising edge of at least one of the electric DC field barriers is preferably not constant in a substantial portion of the rising edge.

In another embodiment, the system can further comprise at least one mass analyzer located downstream of the trapping ion mobility separator. The mass analyzer can be one of an orthogonal time-of-flight mass analyzer, a quadrupole filter, an RF ion trap, an electrostatic ion trap and an ion cyclotron resonance mass spectrometer and it is located downstream of the ion mobility analyzer. The system can further comprise a fragmentation cell located between the trapping ion mobility analyzer and a mass analyzer. The fragmentation cell can be configured to fragment ions by one of collisional induced dissociation (CID), photon induced dissociation (PID), electron capture dissociation (ECD) and electron transfer dissociation (ETD). An additional mass analyzer can be located between the trapping ion mobility separator and the fragmentation cell for selecting precursor ions. The ion source of the system can, for example, be one of an electrospray ion source (ESI), a chemical ionization ion source (CI), a matrix-assisted laser desorption/ionization ion source (MALDI) and an electron impact ion source (EI).

DETAILED DESCRIPTION

The present invention provides an ion mobility spectrometer of the type described in document U.S. Pat. No. 7,838,826 B1 (M. A. Park, 2008), additionally equipped with an upfront RF ion trap operated as an accumulation unit. The accumulation unit operates in parallel with the trapping ion mobility separator, preferably implemented as a separator tunnel. That is, while the trapping ion mobility separator is being used to analyze a first group of ions according to ion mobility, the accumulation unit is simultaneously collecting a second group of ions from an ion source. This second group is then rapidly transferred—in about a millisecond to the trapping ion mobility separator once the analysis of the first group is complete. This allows the accumulation unit to collect ions nearly continuously while the trapping ion mobility separator analyzes ions nearly continuously. In a first preferred embodiment, the accumulation unit is located between an entrance funnel and a separation tunnel. In a second embodiment, the entrance funnel itself can be designed to serve as the accumulation unit. In a third embodiment, the accumulation unit is located upstream of the entrance funnel.

Particularly, in the case of the first embodiment with the accumulation unit located between the entrance funnel and the trapping ion mobility separator, the accumulation unit is preferably designed identical to the trapping ion mobility separator (scan unit), just doubling the scan unit with segmented diaphragm electrodes for generating a quadrupole RF field, and doubling the voltage supply units (with voltage dividers) for generating two independent axial DC electric field barriers. The rising edge of the electric field barrier may not increase as a single linear ramp, but may show a flatter gradient near the top of the barrier, to decompress the density of ions of low mobility. This decompression may be used in both axial DC electric field barriers, in the accumulation barrier and in the scan barrier, to reduce losses of ions. Experience shows that the transfer of ions by the gas flow from the accumulation unit to the scan unit of the device only needs a single millisecond. The delivery of further ions from the ion source need never be stopped. If the accumulation time can be increased to about 300 milliseconds, also a scan time of 300 milliseconds can be used, resulting in a high mobility resolution of $R_{mob} \approx 120$. If no ions get lost in the accumulation unit and scan unit, the utilization of ions amounts to 100 percent.

The accumulation unit must not necessarily be identical with the scan unit of the device. As an example, ions can be accumulated in an octopole or hexapole RF field, instead of a quadrupolar one. Hexapole and octopole RF fields can take up more ions. They can be made shorter than the scan unit, because it is useless to collect more ions than can be held in the scan unit of the device.

Figure 1:
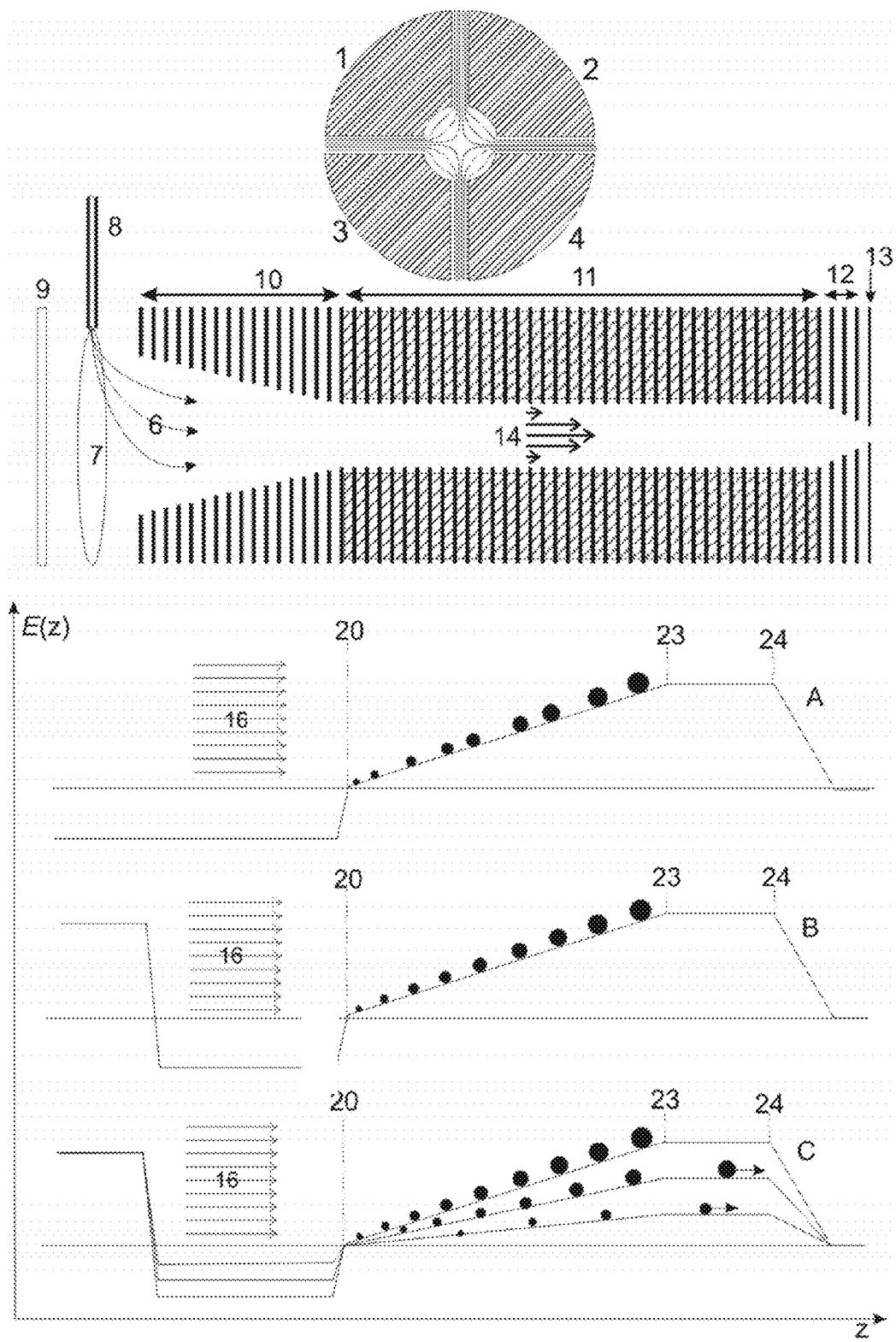
FIG. 1 schematically illustrates the design and operation of an ion mobility spectrometer according to prior art, as described in U.S. Pat. No. 7,838,826 B1 (M. A. Park, 2008).

If the entrance funnel (10) of FIG. 1 is used as the accumulation unit, only small design changes need to be made to adapt its size and function to take up sufficient ions for the subsequent mobility analysis. An accumulation unit located upstream of the entrance funnel can be designed as a common RF linear ion trap comprising a quadrupole, hexapole or octopole RF rod system.

Figure 2:
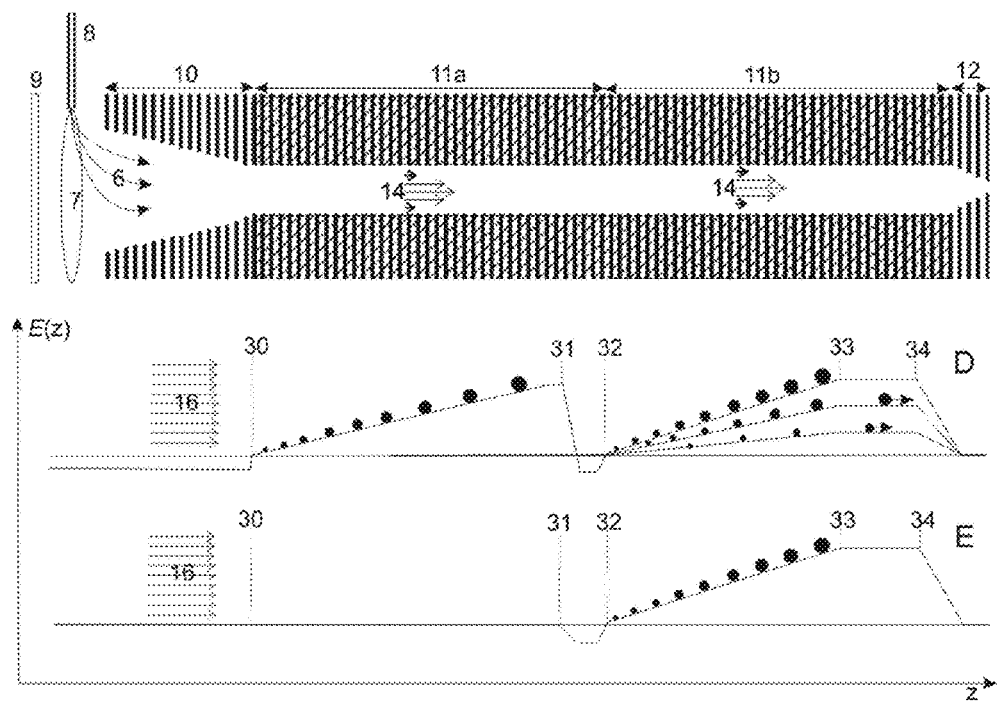
FIG. 2 shows an embodiment of a mobility spectrometer according to the present invention, with an elongated tunnel (11), divided into an accumulation unit (11a) and a scan unit (11b), and two voltage supply units (not shown) for the two tunnel units (11a, 11b), contacting the diaphragms at locations (31) and (34). Chains of resistors between the diaphragms in both tunnel units produce two axial electric DC field profiles, shown in the bottom part of the figure. The operation comprises two phases: In the accumulation and scan phase (D), ions from an ion source (not shown) are accumulated on the rising edge of the electric field profile in the accumulation unit (11a) while, at the same time, ions in the scan unit (11b) are scanned by decreasing the voltage supplied to location (34) of the scan unit (11b), thereby releasing ions with higher and higher mobilities through the exit funnel (13) towards the ion detector. In the transfer phase (E), first the voltage of the scan unit (11b) is restored, and then the voltage of the accumulation unit (11a) is switched off to let the ions be driven by the gas flow onto the rising edge of the electric field profile of the scan unit (11b). The transfer is completed after only one millisecond, and the accumulation and scan phase may start again by switching on the voltage at location (31).

FIG. 2 shows an embodiment with an accumulation unit (11a) between an entrance funnel (10) and separator tunnel (11b). The accumulation unit (11a) is designed identical to the mobility separator tunnel (11b) (scan unit), just doubling the separator tunnel (11b) with its segmented diaphragm electrodes for generating a quadrupolar RF field, and doubling the voltage supply units (with voltage dividers) for generating two independent axial DC electric field barriers in series. In the lower part of FIG. 2, the field profiles for the two operation phases are shown; the accumulation and scan phase (D), and the ion transfer phase (E).

Figure 3:
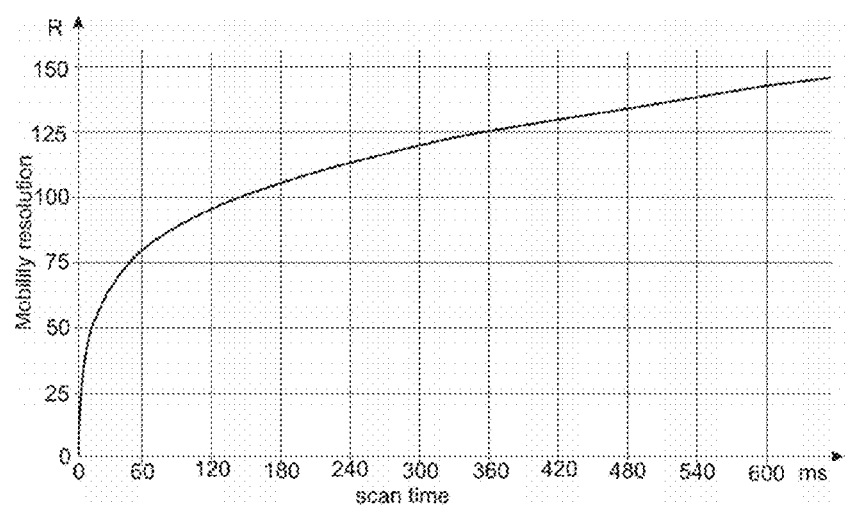
FIG. 3 shows the dependence of the mobility resolution R for the device shown in FIG. 1, given for ions of low mobility ($K_0 \approx 0.5$ cm$^2$/Vs), on the scan time $t_s$. The scan time $t_s$ comprises the full scan from low mobility ($K_0 \approx 0.5$ cm$^2$/Vs) to high mobility ($K_0 \approx 1.0$ cm$^2$/Vs). Usually, the general interest is on ions of low mobility because they show the highest variety of folding states. A scan time of 60 milliseconds over the full range of mobilities achieves a mobility resolution of R$\approx$80; a mobility resolution of R$\approx$125 needs a scan time of 360 milliseconds.

In FIG. 2, both rising edges (ramps) of the field profile are linear, which can result in an unfavorable high density of ions with low mobilities near the top of the profile leading to high losses of these ions due to Coulomb repulsion ("space charge effect"). With long accumulation times, the high mass ions, usually having low mobilities because of their high cross sections, get lost first because they are much less strongly focused by the pseudo-potential within the quadrupolar RF field than low mass ions, showing high mobility due to their lower cross section. The effective force corresponding to the pseudo-potential is proportional to $z^2/m$, z being the number of elementary charges of the ion, and m their mass. High mass ions are only weakly focused, and thus are more sensitive to space charge repulsion, driving the ions radially out of the device. With standard high performance electrospray ion sources, severe losses of high mass ions already start with accumulation times above 40 milliseconds. If the accumulation and scan times are restricted to only 40 milliseconds, the mobility resolution is restricted to only $R_{mob} \approx 65$, because the mobility resolution of a trapping ion mobility spectrometer depends on the scan time $t_s$. The scan time $t_s$ is defined here as the time needed to scan over a common mobility range from low mobility ($Ko \approx 0.5$ cm$^2$/Vs) to high mobility ($Ko \approx 1.0$ cm$^2$/Vs). The dependence of the mobility resolution on the scan time is shown in FIG. 3. Since the mobility resolution $R_{mob}$ also depends on the mobility K itself, the dependence is shown for ions with $Ko \approx 0.5$ cm$^2$/Vs.

To overcome losses of high mass ions, the present invention further proposes to decrease the density for low mobility ions near the summit, and to accept a higher density of high mobility ions near the foot of the axial DC electric field barrier. This goal can be achieved by a non-constant gradient (slope) of the electric field E(z) at the rising edge of the axial DC electric field barrier. A preferred embodiment is given by the profile in part (F) of FIG. 4. Here, the electric field increases non-linearly according to the function $E(z) \sim z^p$, with an exponent $p=\frac{2}{3}$. This form of field ramp decreases the field gradient near the summit, decompressing the high mass ion density, and increases the field gradient near the foot, compressing the low mass ion density. The value $p=\frac{2}{3}$ is only an example; in fact, p may assume any value smaller than 1.0. A favorable range for the exponent p is $0.3 \leq p \leq 0.9$. If the mixture of ions contains many high mass ions, a value of $p=\frac{1}{2}$ may be more favorable; in the extreme, even $p=\frac{1}{3}$ may serve the purpose best.

Figure 5:
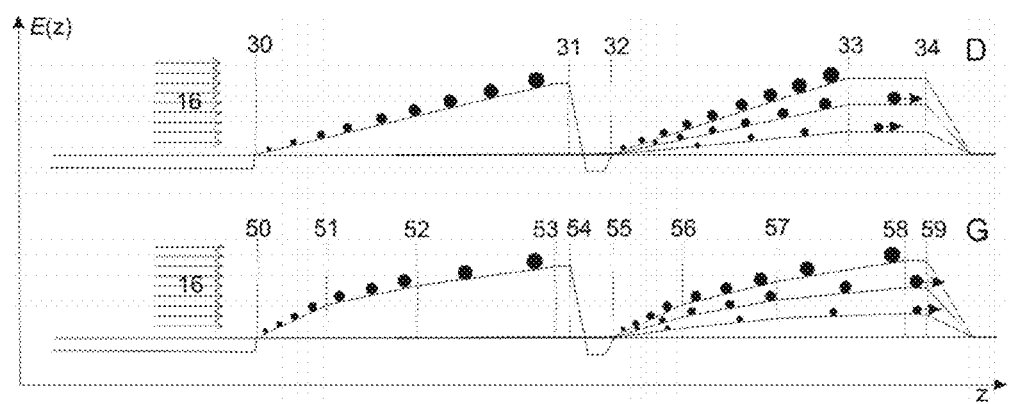
FIG. 5 again shows two different profiles of the electric field. In the upper part (D), repeated for reasons of comparison from FIG. 2, the electric field strength increases linearly along the axis z of the device. Below, in part (F), the ramp of the electric field shows, in the accumulation unit as well as in the scan unit, three linear field gradients. In the accumulation profile, the linear field gradients are located between z locations (50) and (51), (51) and (52), and (52) and (53) respectively, the lowest gradient near the top. In the scan profile, the linear field gradients are positioned between z locations (55) and (56), (56) and (57), and (57) and (58) respectively. Near both tops, ion density and space charge are diminished, compared with the profile in part (D) at the top. In the second field profile, a further decompression of ions is achieved by a shorter length $L_p$ of the plateau.

Another embodiment of the invention is shown in part (G) of FIG. 5, showing a piecewise linear increase with three different gradients of the electric field. The field gradient between z positions (52) and (53), and between (57) and (58) near the top are flattest, decompressing the ions with low mobility and reducing the space charge repulsion. Of course, more than just three gradients may be applied.

In another embodiment, the electric field profiles are adjusted with respect to the ion density in the mobility spectrum determined in one or more preceding measurements. As an example for a variable field profile, the gradients of the piecewise linear parts of the rising edge, as shown in part (G) of FIG. 5, can be varied by two voltage generators delivering each three adjustable voltages $V_{51}$, $V_{52}$ and $V_{54}$, and $V_{56}$, $V_{57}$ and $V_{59}$, which are applied to diaphragms at corresponding positions on the z axis. By adjusting, for example, the voltages $V_{51}$ and $V_{52}$ relative to voltage $V_{54}$, a variety of field profiles for the accumulation unit can be generated. If a preceding measurement shows a high density of low mobility ions, the field gradient between positions (52) and (53) can be made as flat as necessary to avoid losses. The preceding measurement can also be used to adjust the field profile of the scan unit. As a matter of course, more adjustable voltages may be used at more z positions.

With a more complex device, voltages at all or a large part of the diaphragms along the z-axis may be generated by a series of digital-to-analog converters (DAC). Then, any field profile can be generated, enabling an operation which reacts exactly to any density distribution of ions on the mobility scale.

Figure 4:
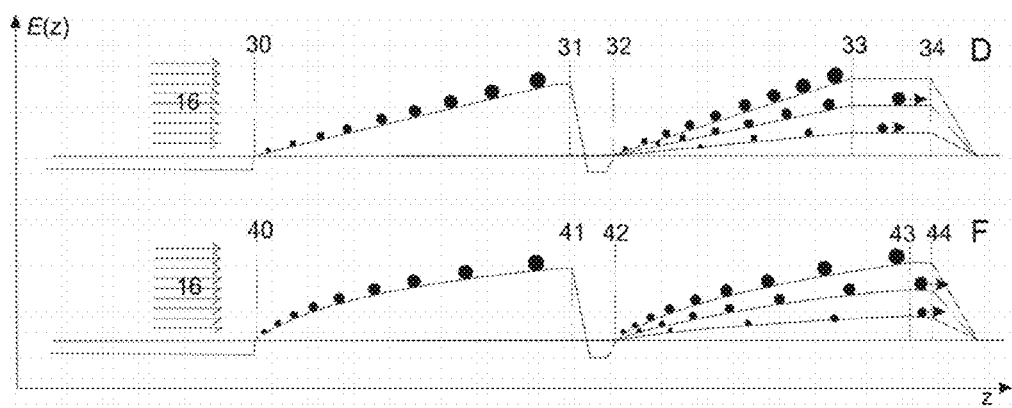
FIG. 4 shows two different profiles of the electric field, generating different ion densities near the top of the electric field profile. In the upper part (D), repeated from FIG. 2, the electric field strength increases linearly along the z-axis of the device, showing equal ion density along the ramp, in case a mixture of ions with uniform mobility distribution is provided. In the bottom profile (F), the electric field increases proportionally to $z^{2/3}$. As indicated by the dots, high mass ions near the top of the ramp are uncompressed by the field proportional to $z^{2/3}$, whereas low mass ions are compressed at the foot of the ramp. Near the top of the ramp, the space charge is diminished, and losses of high mass ions are considerably reduced.

For reason of comparison, the upper parts (D) of FIGS. 4 and 5 show a field ramp of linear increase, where it is to be seen that the ions of a mixture having a uniform mobility distribution are uniformly distributed along the rising edge. In practice, however, the mobilities of ions are rarely uniformly distributed.

Experience shows that the transfer of ions by the gas flow from the accumulation unit to the scan unit of the device only needs some millisecond or less when the gas has a velocity of about 100 m/s at a pressure of some millibar. The delivery of further ions from the ion source need never be stopped. If the accumulation time can be increased to about 300 milliseconds without major losses of ions, a scan time of 300 milliseconds can be used, resulting in a high mobility resolution of $R_{mob} \approx 120$. If no ions get lost in the accumulation unit and scan unit at all, then the duty cycle would be to 100 percent.

The accumulation unit of the device must not necessarily be identical in design with the scan unit. As an example, the ions can be accumulated in an octopole or hexapole RF field, instead of a quadrupolar one. Hexapole and octopole fields can take up more ions. Segmented diaphragms for generating hexapole or octopole RF fields may be designed similar to the segmented diaphragms (1, 2, 3, 4) used for the scan unit (11b), only with more radial electrode segments. Because it is useless to collect more ions than can be held in the scan unit (11b) with a quadrupolar RF field, the multipole accumulation unit can be made shorter.

In case an entrance funnel is used as accumulation unit, only small design changes need to be made to the setup shown in FIG. 1 in order to accumulate a sufficient number of ions from the ion source. The funnel (10) can be made longer to increase its volume, and an additional voltage supply unit may deliver a switchable repelling DC potential (stopping voltage) to the last diaphragm of the funnel (10).

An accumulation unit upstream of the entrance funnel can be implemented as a common linear RF ion trap comprising a quadrupole, hexapole or octopole RF rod system. Storage devices of this type are well-known to the specialist in the field and need not be further described here.

It should be mentioned that the scan need not necessarily be performed by linearly decreasing the voltage for the field profile. In the U.S. Pat. No. 8,766,176 B2 (M. A. Park et al, 2011), different scan modes are presented. In particular, a scan mode with a partial slow scan speed can increase the mobility resolution for ions in a smaller range of mobilities. A "zoom scan" consists of three phases: a first partial scan with highest scan speed, a second "zoom" phase with a reduced scan speed for highest resolution, and a third phase with fast scan speed to empty the trap.

It goes without saying that the capacity of the accumulation and scan units also can be increased by enlarging the inner diameter of the device. A larger ion mobility spectrometer with higher RF voltages may still be acceptable for a mass spectrometer, but the gas flow, increasing with the fourth order of the inner diameter, needs much bigger and more expensive vacuum pumps.

The invention claimed is:

1. A method for operating a trapping ion mobility spectrometer, comprising the steps:
   (a) accumulating ions from an ion source in an RF ion trap;
   (b) transferring at least a subset of the accumulated ions into a trapping ion mobility separator, in which the transferred ions are radially confined by an RF field and pushed by a gas flow against a rising edge of an axial electric DC field barrier such that the transferred ions are spatially separated along the rising edge according to ion mobility;
   (c) successively releasing the transferred ions according to their ion mobility by decreasing the height of the electric DC field barrier while ions from the ion source are further accumulated in the RF ion trap; and
   (d) restoring the height of the electric DC field barrier which triggers a consecutive transfer of the accumulated ions from the RF ion trap into the trapping ion mobility separator.

2. The method according to claim 1, wherein the ions are radially confined by a quadrupolar RF field in the trapping ion mobility separator.

3. The method according to claim 2, wherein the ions are accumulated in a linear RF trap.

4. The method according to claim 3, wherein the accumulated ions are radially confined in the linear RF ion trap by one of quadrupolar, hexapolar and octopolar RF field.

5. The method according to claim 2, wherein the ions are accumulated in a RF funnel wherein the field at the exit of the RF funnel is adjusted to the quadrupolar RF field at the entrance of the trapping ion mobility separator.

6. The method according to claim 1, wherein, during steps (a) and (c), ions are axially trapped at the exit of the RF ion trap by applying a repelling DC potential to an exit electrode of the RF ion trap.

7. The method according to claim 1, wherein steps (b) and (c) are repeated to acquire a series of ion mobility spectra.

8. The method according to claim 7, wherein the ion density is determined as a function of ion mobility from one or more preceding ion mobility spectra and the electric field profile of the rising edge of the first electric DC field barrier is adjusted to minimize ion losses in the trapping ion mobility separator during steps (b) and (c).

9. A method for operating a trapping ion mobility spectrometer, comprising the steps:
   (a) accumulating ions from an ion source in an RF ion trap;
   (b) transferring at least a subset of the accumulated ions into a trapping ion mobility separator, in which the transferred ions are radially confined by an RF field and pushed by a gas flow against a rising edge of a first axial electric DC field barrier such that the transferred ions are spatially separated along the rising edge according to ion mobility; and
   (c) successively releasing the transferred ions according to their ion mobility by decreasing the height of the first axial electric DC field barrier while ions from the ion source are further accumulated in the RF ion trap, wherein, during steps (a) and (c), ions in the RF ion trap are pushed by the gas flow in the axial direction against a rising edge of a second axial electric DC field barrier wherein the height of the second axial electric DC field barrier is adjusted such that ions are trapped along the rising edge of the second axial electric DC field barrier and spatially separated according to ion mobility.

10. The method according to claim 9, wherein, in step (b), ions are transferred into the trapping ion mobility separator by reversing, turning-off or decreasing the height of the second axial electric DC field barrier.

11. The method according to claim 9, wherein the ion density is determined as a function of ion mobility from one or more preceding ion mobility spectra and the electric field profile of the rising edge of the second axial electric DC field barrier is adjusted to minimize ion losses in the RF ion trap during steps (a) and (c).

12. The method according to claim 9, wherein the transferred ions are further analyzed in a mass analyzer being located downstream of the trapping ion mobility separator.

13. The method according to claim 9, wherein the transferred ions are fragmented in a fragmentation cell located downstream of the ion trapping mobility separator and the fragments ions are analyzed in a mass analyzer.

14. A system comprising:
an ion source;
an RF ion trap; and
a trapping ion mobility separator comprising an RF field for radially confining ions, an axially acting electric DC field barrier having a rising edge with an increasing electric DC field and a gas flow counteracting the electric DC field at the rising edge;
wherein the RF ion trap is located between the ion source and the trapping ion mobility separator and wherein the RF ion trap has a first mode of operation for accumulating ions from the ion source and a second mode of operation for transferring ions towards the ion trapping ion mobility separator; and
wherein the RF ion trap comprises an axially acting adjustable electric DC field barrier having a rising edge with an increasing electric DC field and a gas flow counteracting the electric DC field at the rising edge.

15. The system according to claim 14, wherein the RF ion trap is an RF funnel.

16. The system according to claim 14, wherein the RF ion trap is a linear RF ion trap which is aligned along a common axis with the trapping ion mobility separator and wherein both, the linear RF ion trap and the trapping ion mobility separator comprise a tube for radially confining the gas flow along the common axis.

17. The system according to claim 14, wherein the slope (axial gradient) of the electric field strength along the rising edge of at least one electric DC field barrier is not constant at a substantial portion of the rising edge.

18. The system according to claim 17, wherein the radially confining RF fields of the linear RF ion trap or the trapping ion mobility separator are substantially quadrupolar.

19. The system according to claim 14, further comprising at least one of a fragmentation cell and a mass analyzer located downstream of the ion mobility separator.

20. The method according to claim 1, wherein the transferred ions are further analyzed in a mass analyzer being located downstream of the trapping ion mobility separator.

21. The method according to claim 1, wherein the transferred ions are fragmented in a fragmentation cell located downstream of the ion trapping mobility separator and the fragments ions are analyzed in a mass analyzer.

* * * * *